United States Patent [19]
Webster

[11] Patent Number: 5,648,530
[45] Date of Patent: Jul. 15, 1997

[54] MANUFACTURE OF CARBONYL FLORIDE

[76] Inventor: James Lang Webster, 202 N. Hills Dr., Parkersburg, W. Va. 26101

[21] Appl. No.: 573,677

[22] Filed: Dec. 18, 1995

Related U.S. Application Data

[63] Continuation-in-part of Ser. No. 510,060, Aug. 1, 1995, abandoned, which is a continuation-in-part of Ser. No. 362,355, Dec. 22, 1994, abandoned.

[51] Int. Cl.$^6$ .................................................. C07C 51/58
[52] U.S. Cl. ................................... 562/849; 562/852
[58] Field of Search ..................................... 562/849, 852

[56] References Cited

U.S. PATENT DOCUMENTS

| | | | |
|---|---|---|---|
| 2,709,189 | 5/1955 | Farlow et al. | 260/653 |
| 2,757,214 | 7/1956 | Muetterties | 260/653 |
| 3,322,823 | 5/1967 | Langer | 260/544 |

FOREIGN PATENT DOCUMENTS

| | | | |
|---|---|---|---|
| 208251 | 1/1981 | Czechoslovakia | C01B 9/08 |
| 2124621 | 9/1972 | France | B01J 1/00 |

OTHER PUBLICATIONS

Farlow et al., Carbonylfluoride, *Industrial Inorganics*, 18–0657, pp. 155–158, 1965.

Pola et al, Simultaneous Production of Carbonyl fluoride and sulfur tetrafluoride, *Industrial Inorganics*, 96, 159, 1982.

*Primary Examiner*—Paul J. Killos

[57] ABSTRACT

Carbonyl fluoride is produced by reacting fluorine-containing compound such as metal fluoride with CO in an excited state, such as produced by a plasma, to obtain a gaseous reaction mixture, which can then be quenched to obtain the $COF_2$.

19 Claims, No Drawings

MANUFACTURE OF CARBONYL FLORIDE

This application is a continuation-in-part of U.S. patent application Ser. No. 08/510,060, filed Aug. 1, 1995, abandoned which is in turn a continuation-in-part of U.S. patent application Ser. No. 08/362,355, filed Dec. 22, 1994 and now abandoned, all filed by the same inventor.

FIELD OF THE INVENTION

This invention relates to process for the manufacture of carbonyl fluoride.

BACKGROUND OF THE INVENTION

Carbonyl fluoride ($COF_2$) is useful for example as an intermediate to make fluorocarbons such as tetrafluoroethylene (TFE), such as disclosed in U.S. Pat. No. 2,709,189. U.S. Pat. No. 2,757,214 discloses the reaction of calcium fluoride with phosgene ($COCl_2$) at temperatures up to 1000° C. to produce perhalomethane. Additional products produced are COFCl and $COF_2$. The patent also discloses that the phosgene may be formed in situ by combining CO and Cl under pressure at the reaction temperature. Example X discloses the formation of the phosgene reactant in situ using excess CO and reports the obtaining of 2 mol % $COF_2$ (plus the possible loss of some $COF_2$ to account for the presence of 5 mol % SiF4) along with 13 mol % COFCl, 20 mol % $CO_2$, 1 mol % perhalomethane and 1 mol % of HCl. Because of low yield of $COF_2$ and attendant large yield of virtually useless other products, this process has not been used commercially for the manufacture of $COF_2$.

U.S. Pat. No. 3,322,823 discloses another method of forming $COF_2$, namely by reacting a mixture of Group I-A or II-A metal fluoride with carbon and an oxide of a metal which is reducible in the presence of the carbon in a crucible forming the anode of an electric arc furnace. The $COF_2$ volatilizes from the molten reaction mass and is collected in a liquid nitrogen trap. The reaction scheme is as follows:

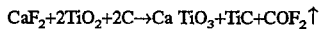

$CaF_2 + 2TiO_2 + 2C \rightarrow Ca\ TiO_3 + TiC + COF_2 \uparrow$

This process has the disadvantages of operation to create a molten mass within an electric arc furnace, which is cumbersome and therefore expensive, and the calcium and titanium byproducts created in large amount having little to no value.

$COF_2$ has been made commercially by reacting $COCl_2$ with HF, thus obtaining HCl as a byproduct. This process has the disadvantage of the expense of making the phosgene reactant and the cost of disposal of large amounts of HCl.

A more economical process for making $COF_2$ is needed.

SUMMARY OF THE INVENTION

The present invention satisfies this need by the process of reacting fluorine-containing compound having a molecular weight greater than 20 with carbon monoxide (CO) to obtain carbonyl fluoride in high yield. When the fluorine-containing compound is metal fluoride, the other major reaction product (metal from the metal fluoride) can be recovered and the value of this metal can further reduce the cost of the process. Thus the reaction can be depicted by the following equation:

metal fluoride+CO→$COF_2$+metal　　(1)

Similar recovery can be carried out when the fluorine-containing compound has other moieties of value.

The reaction is carried out by energizing the fluorine-containing compound and/or the CO and/or an inert gas, such as by forming a plasma of one or more of these materials, which provides a gaseous reaction mixture of dissociated species and possibly $COF_2$, depending upon reaction conditions. The dissociated species are a precursor to $COF_2$. In any event, quenching of this reaction mixture provides the $COF_2$. When the fluorine-containing compound is metal fluoride, the metal is separable from the $COF_2$ by virtue of the metal being normally solid at ambient conditions while the $COF_2$ is gaseous at these conditions. The process can be conducted so that few byproducts are formed, thereby minimizing waste disposal costs, yet with the potential for the metal byproduct or other formed byproduct to have value.

DETAILED DESCRIPTION OF THE INVENTION

With respect to the starting materials of the process of the present invention, the CO can be obtained commercially or it can be created in situ by feeding $O_2$ and C to the reactor, preferably with the conversion to CO being completed prior to contact with the fluorine-containing compound, so that oxygen from the oxygen feed is no longer present for reaction with any portion of the fluorine-containing compound. Any compound which provides fluorine to the reaction with CO can be used. Preferably, however, the compound is free of hydrogen and any other halogen atom. The requirement that the compound have a molecular weight of greater than 20 excludes HF as a suitable compound. Since $F_2$ is not a compound, it too is excluded as a feed material to the reactor. The compound serving as the source of fluorine can be organic or inorganic, the latter being preferred because inorganic compounds are naturally occurring or are obtained by processing naturally occurring compounds, wherein the fluorine-containing compound may be a by-product of such processing and will typically be non-carbonaceous. Organic fluorine-containing compounds may also have by-product sources, and indeed, could be from the recycle by-product stream obtained from the process of the present invention.

The fluorine-containing compound can be a compound or a mixture of compounds, i.e., at least one fluorine-containing compound. It is the fluorine atoms that are the reactive portion of the compound, whereby the remaining portion of the compound can have a wide range of identities. It is only necessary that the fluorine-containing compound provide fluorine to the reaction, which is generally accomplished by the compound liberating fluorine under reaction conditions involving heat. With respect to metal fluoride as the preferred fluorine-containing compound, the metal can be selected from elements in Groups IA, excluding hydrogen, IB, IIA, IIB, IIIA, IIIB, IVA, VA, excluding nitrogen, VB, VIA, excluding oxygen, VIB, VIIB, and VIII of the Periodic Table (R. H. Perry and C. H. Chilton, *Chemical Engineers' Handbook*, 5th Edition, McGraw-Hill, inside cover (1973). Preferably, the metal portion of the metal fluoride has inertness or low reactivity to the CO reactant under the conditions of the reaction and the reaction conditions are such that the fluorine atoms which leave the fluorine-containing compound during the reaction do not return to reform the compound, e.g., the metal fluoride. Such reaction conditions can include rapid cooling of the reaction mixture so that the fluorine split off from the fluorine-containing compound more stably combines with the CO moiety so as to be unavailable to return. The fluorine-containing compound, including metal fluoride, can be simple or complex, e.g., containing two cations and one anion, such as fluorine-containing complex salts. Examples of metal fluorides include sodium fluoride, magnesium fluoride, and sulfur fluoride. Preferred fluorides because of low cost include $CaF_2$ and silicon fluoride such as $SiF_4$, $Si_2F_6$, and metal silicon fluorides (fluorosilicates) such as calcium fluorosilicate. Additional metal fluorides include fluoroborates, fluorophosphates, and cryolite ($Na_3AlF_6$). Examples of organic fluorides include $CF_4$, $C_2F_6$, and perfluoroolefins such as tetrafluoroethylene and hexafluoropropylene.

The reaction between fluorine-containing compound and CO is in the gaseous state and includes the removal of the fluorine atoms from the fluoride-containing compound. Thermodynamically, as an equilibrium reaction, the reformation of the fluoride-containing compound, such as metal fluoride, is to be expected. To make the dissociation reaction occur, however, the reactants are exposed to sufficient energy which is effective to energize the feed material, i.e., to cause dissociation of at least a portion of at least one of the reactants in the reaction zone. This dissociation can be into radicals, atoms, and/or ions, which in essence is the excited state for the molecules of the feed material. In a sense, the reaction is being initiated by dissociation energy being present in the reaction zone. Although the reaction may be occurring between radicals, atoms, and/or ions, the reaction can simply be described as the reaction between the fluorine-containing compound such as the metal fluoride, and CO. The effect of the excited state of the feed material is that the fluorine from the fluorine-containing compound is free to combine with the CO in some way in the gaseous reaction mixture. Measures to maintain this combination so that the fluorine does not recombine with the remainder of the compound such as the metal will be described later herein.

The description of the present invention herein having revealed the starting materials and reaction mechanism to be used, one skilled in the art will recognize many ways to expose (subject) the reactants to the dissociation energy required. Thus, the reaction can be carried out by producing the dissociation energy by an electrical arc, either A.C. or D.C., using a plasma reactor or by other equipment which produces electromagnetic energy, such as an induction coil. In the case of the electric arc, the applicator of the dissociation energy is within the reaction zone, while in the case of the induction coil, the applicator of the electromagnetic energy, can be exterior to the reaction zone, but creating the dissociation energy within the zone.

A plasma reactor is one type of apparatus for carrying out the metal fluoride/CO reaction by plasma excitation. This type of energy generator includes a pair of electrodes which generates an arc from electrical current passing from one electrode to the other. An electrical discharge between these electrodes can be rotated by a coil-induced magnetic field or the arc can be stationary. The electrodes can be of copper and water cooled so as to provide long operating time. It is the region of the arc that provides the dissociation energy useful in the present invention, in this case both electrical energy and the thermal energy generated by the electrical current. The arc region produces a plasma of material fed to it and which dissociates upon exposure to the arc, and this in turn can produce a glow region extending downstream from the arc, in the direction of the fluid flow within the reactor, which glow area is called the plasma flame. The temperature produced by the arc can be controlled by varying the power input and/or material feed. For the particular power available from the reactor, the flow rate of the feed material is adjusted so that the feed material becomes energized (excited) by this exposure to dissociation energy. Measures can be taken, e.g., a rotating electric arc, to produce a turbulent mixing action in the reaction zone and within the arc, to give high operating efficiency and prolonged electrode life.

Each of the feed materials can be directly or indirectly energized, i.e., exposed (subjected) to the dissociation energy generated by the electric arc or by other means. An example of direct exposure would be when all of the reactants are fed to the electrical arc (or the electromagnetic field of different apparatus). An example of indirect exposure would be when only one of the reactants is in the arc (direct exposure), and the resultant dissociated reactant is then brought into contact with the other reactant (indirect exposure) downstream from the arc, within the plasma flame. Another example of indirect exposure would be when an inert gas such as argon is directly exposed to the arc or electromagnetic field to cause a portion of the argon to dissociate, and the resultant argon is then brought into contact with the reactants. The plasma flame is formed from the particular feed material that is directly exposed to the arc in the plasma reactor, but the flame may also envelop the feed material(s) brought into contact with the plasma downstream from the arc. Thus, the present invention includes all of these possibilities for exposing the feed materials to dissociation energy (energizing of the feed materials) in the reaction zone or as stated above, energizing the feed material to step (a) of the process. These possibilities can be effective to prolong electrode life in the case when one or more of the feed materials are corrosive to the electrode. Thus CO may be the only reactant fed to the electrode region, or inert gas such as argon may be fed to the electrode region instead on any of the reactants.

The combination of electrical and thermal energy used to energize the feed material can generally be quantified by specification of the power input to the reaction zone. Thermal energy may also be provided by preheating one or more of the materials fed to the reaction zone. The reaction zone includes the region of the electric arc or electromagnetic energy in which the plasma is initially developed and the region in which the feed materials are brought together.

The temperature in the electric arc or electromagnetic field will be varied by varying power input and/or feed material flow rate depending on the particular fluorine-containing reactant and pressure within the reaction zone to cause the formation of a plasma flame. In the case of metal fluoride reactants, fluorine is most tightly bound to such metals as silicon, magnesium, calcium, and aluminum, and less so to metals such as iron, copper, zinc, and silver. In general, less energy (lower temperature) is required to dissociate the metal fluoride when the metal/fluorine bond is weaker. For any particular metal fluoride or other fluorine-containing compound, lower pressure within the reaction zone, allows the dissociation to occur at lower the temperature. The pressure can be sub-atmospheric, atmospheric, or super-atmospheric. By way of example of the effect of pressure, if carbon tetra fluoride were fed to the reaction zone, the level of dissociation at atmospheric pressure and 2700° C. would be similar to that obtained at 10 mm Hg and 2200° C.

For the range of fluorine-containing compound, e.g., metal fluoride, starting materials that can be used, along with the range of pressures that can be used, it is believed that when heat is present in the creation of the dissociation energy, the temperature where the reactants come together in the reaction zone will be at least sufficient to liberate fluorine from the fluorine-containing compound. Generally, at least 1500° C. at atmospheric pressure will be required, but lower temperatures may be used at subatmospheric pressures. More often, the temperature will be at least 3500° C. and preferably at least 4500° C. at atmospheric pressure. Extremely higher temperatures may be used, e.g., up to 5000° C. or up to 6000° C. or even more than 10,000° C., at which temperatures, all reactants could be dissociated. At such temperatures, the fluorine-containing compounds, e.g., metal fluorides, if not gaseous at ambient temperature, are either completely or partially volatilized in the reaction zone. The temperature to which the fluorine-containing compound, e.g., metal fluoride, is exposed in the reaction zone may be sufficient to cause the metal fluoride to dissociate into metal ions and fluoride ions, but may or may not cause substantial dissociation of the CO. The metal fluoride or other fluorine-containing compound may be exposed to a higher temperature e reaction zone than the CO by having the metal fluoride be exposed to the maximum dissociation energy present, the arc in the case of a plasma reactor, and then bringing the at least partially dissociated metal fluoride or other fluorine-containing compound into contact with the CO at a lower temperature, e.g., within the plasma flame created by the energized metal fluoride. The temperature of the plasma flame decreases with increasing distance from the source of the flame, e.g., the plasma torch. Introduction of the CO reactant to the flame downstream from the torch and the point(s) of introduction of the fluorine-containing compound to the flame provides for reaction of the CO with dissociating fluorine-containing compound, but essentially no dissociation of the CO reactant. Depending on the temperature of the flame at the point of CO introduction and the amount of CO introduced, the CO may also quench the plasma flame while simultaneously reacting with fluorine from the dissociated fluorine-containing compound. Preferably, the CO is less than 20% dissociated, more preferably, less than 10% dissociated, and even more preferably is almost entirely molecular CO at the time of reaction.

Silicon tetrafluoride is gaseous at ambient conditions and thus provides a convenient feed to the reaction zone, wherein both reactants fed to the reaction zone are gaseous. $CaF_2$, e.g., boils at 2500° C. and can therefore be present as a gas or mixture of gas and solid or liquid in the reaction zone, depending on the temperature and pressure in this zone. The metal fluoride or other fluorine-containing compound may even be present as a mixture of gas and solid material, again depending on the particular fluorine-containing compound. Temperatures of about 2000° C. and less can conveniently be measured with a thermocouple. Higher temperatures, especially those of an electrical arc or plasma flame can be determined by known means, such as is determined from such parameters as power inputs, feed compositions, flow rates, and measurement of heat losses or as determined from emission spectroscopy.

The proportion of CO in the feed to the reaction zone is preferably sufficient to combine with the fluorine atoms of the fluorine-containing compound so that fluorine atoms are not left over to recombine to re-form the fluorine-containing compound, e.g., metal fluoride. This is not to say that all of the fluorine-containing compound fed to the reaction zone will react with the CO in a single pass through this zone. It may be desirable to react only a portion of the fluorine-containing compound in a single pass through the zone and to recycle unreacted fluorine-containing compound to the reaction zone for further conversion. Preferably, however, the reaction is conducted so that a single pass is sufficient, wherein at least 50% of the metal fluoride or other fluorine-containing compound is stripped of its fluorine and more preferably, at least 85%, and even more preferably, at least 90%. These conversions can also be obtained by recycling unreacted metal fluoride or other fluorine-containing compound.

The principal reaction products present as a gaseous reaction mixture from the metal fluoride (or other fluorine-containing compound)/CO reaction are believed to be metal (or other moiety of other fluorine-containing compound) and some combination of F and CO, possibly in a dissociated state. Quenching of this reaction mixture to a temperature at which $COF_2$ is stable yields $COF_2$. Because the reaction mixture has this capability of forming $COF_2$ upon quenching, the reaction product at the time it is formed, for simplicity, can be considered to be $COF_2$.

The quenching of the reaction mixture can prevent the fluorine atoms from recombining with the remainder of the fluorine-containing compound to reform the compound such as metal fluoride. The presence of excess CO in the reaction tends to drive the reaction towards the formulation of $COF_2$ rather than reformation of the fluorine-containing compound. Removal of the metal from the reaction mixture can also be practiced so that the metal is no longer available for attraction of fluorine from the reaction mixture. The same is true for the other moiety of other fluorine-containing compounds. This can be accomplished by stepwise quenching, first to a temperature at which the metal (or other moiety) becomes non-gaseous, i.e., liquid or solid, which is separable from the remainder of the gaseous reaction mixture. The combination of F and CO and/or $COF_2$ can then be used as such for additional chemical reaction or further quenched to room temperature. Alternatively, the reaction mixture can simply be quenched to ambient conditions, in which case the non-gaseous metal can be easily separable from the desired gaseous $COF_2$ reaction product. All of these measures maintain the combination of F and CO so that the reaction product upon quenching is $COF_2$.

$CF_4$ can be formed as a co-product with $COF_2$, but the formation of $CF_4$ can be minimized in several ways. Since CO is more thermally stable than metal fluorides, the use of atmospheric pressure and higher pressure tends to drive the reaction to favor the formation of $COF_2$ rather than $CF_4$. In one embodiment, the heat generated in the reaction, while causing dissociation of the fluorine-containing compound, does not, or only minimally, dissociates the CO. Any formed $CF_4$ is thought to come from the dissociation of CO into carbon and oxygen. Such oxygen is also available to react with the metal formed.

Preferably, at least one molecule of CO is present in the reaction zone for each two atoms of fluorine present and more preferably at least 4 molecules of CO are present/two fluorine atoms. A large excess of CO can be present, e.g., up to 20 molecules of CO/two fluorine atoms. The presence of large excesses of CO increases the need for generation of heat (power) to energize the feed material, and thus can increase the cost of the process. In addition to favoring the fluorine to remain apart from the metal present in the reaction mixture, the use of excess CO tends to drive the reaction towards producing $COF_2$ rather than $CF_4$.

The rapidity of cooling the gaseous reaction mixture also favors the formation of $COF_2$ rather than $CF_4$. Preferred quench rates are at least 1000° C./sec, and even more preferred, at least 10000° C./sec., e.g., 100,000° C./sec and 1,000,000° C./sec. In the two-step quench process, the reaction mixture can be quenched to less than 2000° C., e.g., within the range 1500° C. to 2000° C., at which temperature the metal generally becomes non-gaseous, allowing separation from the gaseous reaction mixture. Quenching can be obtained, e.g., by contacting the gaseous reaction mixture with a cooled surface and/or a gas (or liquid) which may be at ambient temperature. If the $COF_2$ is then desired at ambient conditions, the remainder of the reaction mixture can then be further quenched to that condition, still favoring me formation of $COF_2$ rather than $CF_4$ or metal fluoride.

The yield of $COF_2$ obtainable by the process of the present invention can be at least 60%, based on the conversion of metal fluoride or other fluorine-containing compound, preferably at least 80%, and more preferably at least 90%. The gaseous reaction mixture can also contain unreacted fluorine-containing compound, unreacted CO and small amounts of other byproduct such as metal oxide in the case when metal fluoride is the compound or other moiety. Any high boiling metal fluoride and metal oxide or other by-product can be removed from the gaseous mixture along with the reaction by-product. The CO can be recycled. The $COF_2$ yields (mol %) stated above apply whether the process is conducted as a single pass of the fluorine-containing compound through the reaction zone or unreacted compound, if any, is recycled to the reaction zone, in which case the yield is the ultimate yield of the process.

The $COF_2$ can be removed from the gaseous mixture by quenching the mixture to ambient temperature, followed by such separation methods as distillation. Alternatively, the reaction mixture can be maintained at elevated temperature, with or without removal of unreacted metal fluoride and CO, if any, and/or metal byproduct and used as feed material in additional chemical reaction, such as reaction with carbon to obtain tetrafluoroethylene.

EXAMPLES

Example 1

The desired reaction sequence is as follows:

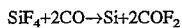

$SiF_4 + 2CO \rightarrow Si + 2COF_2$

The feed in this Example, however, has 400% molar excess of carbon monoxide to help drive the reaction to the desired reaction products shown above. Thus, on a weight basis, 280 g/min of CO are fed between the electrodes of a plasma reactor (e.g., Westinghouse MARC 3 plasma torch) at atmospheric pressure and generating a temperature of about 6000° C. to form a plasma flame of the CO extending downstream from the electrodes. Into this flame are injected 104 g/min of preheated gaseous $SiF_4$ to thereby be mixed with the CO in the flame. The plasma flame extends into a cooled graphite reactor. The temperature in the flame is about 5000° C. The resultant gaseous mixture is quenched to about 1500° C. by contact with a cooled metal wall at a quench rate exceeding 10000° C./sec, and a liquid product separates from the gaseous reaction mix This liquid product is removed from the reactor at a rate of 26 g/min. On solidification at ambient temperature, this product analyzes as 89 wt % Si, 6 wt % oxygen, and 5 wt % fluorine, with the exiting fluorine being a complex (called SiF in Table I) with the silicon metal. This reaction product can be refined to obtain Si at higher purity. Similar results are obtained when the gaseous mixture is quenched at a rate exceeding 10,000° C./sec. to 600° C. using a cooled quench surface, in which case, a solid product separates from the gaseous mixture at a rate of 26 g/min. With additional cooling to ambient temperature (15°–20° C.) elemental analysis by ESCA gives a result similar to that obtained on the liquid product described above.

The remaining gaseous reaction mixture, at 358 g/min, is further cooled (quenched) to ambient temperature if not already at ambient temperature from the quench of the gaseous mixture, and the products therein separated from one another to yield 239 g/min of unconverted CO, 19 g/min of unconverted $SiF_4$, 90 g/min of $COF_2$ and 10 g/min of $CF_4$. Excluding the $SiF_4$ available for recycle, 84% of the fluorine from the $SiF_4$ converted ends up as $COF_2$, 14% as $CF_4$, and $_2$% exited with the liquid metal mixture. The ratio of $COF_2$ to $CF_4$ can be increased by reacting at slightly lower temperatures. The separated CO and unconverted $SiF_4$ are then available for recycle to the reactor.

The material flow rates for this Example are shown in Table I.

TABLE I

| Component | Plasma Feed (g/min) | Liquid Product (g/min) | Exit Gases (g/min) |
|---|---|---|---|
| CO | 280 | | 238.9 |
| $SiF_4$ | 104 | | 19.0 |
| $COF_2$ | | | 90.3 |
| $CF_4$ | | | 10.0 |
| $SiO_2$ | | 3.0 | |
| Si | | 19.6 | |
| SiF | | 3.2 | |
| Total | 384 | 25.8 | 358.2 |

The analyses of the exit gases in this and the other Examples is done by calibrated infrared spectrometry using the following wave numbers: $(cm^{-1})$ for quantitative analysis: CO=2172, $SiF_4$=1030: $COF_2$=1955, and $CF_4$=1281.

Example 2

The desired reaction sequence is as follows:

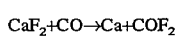

$CaF_2 + CO \rightarrow Ca + COF_2$

The plasma reactor (torch) and graphite reactor described in Example 1 are used in this Example. Again a 400% excess of CO is used to drive the reaction to the desired products. Thus on a weight basis, 135 g/min of CO is fed to the arc electrodes at atmospheric pressure and heated to about 6000° C. Additional CO (about 5 g/min) is used to help aspirate the gravity feed of 78 g/min of powdered preheated $CaF_2$ into the plasma flame downstream from the electrodes, wherein the temperature is about 5000° C. The resultant gaseous reaction stream is quenched at a rate exceeding 10000° C./sec to a temperature below 1000° C., and a solid product at the rate of 48 g/min is removed from the gaseous reaction mixture. Upon cooling to ambient temperature, this solid product is analyzed to contain 62 wt % Ca, 32 wt % $CaF_2$, and 6 wt % CaO. The $CaF_2$ in this solid product accounts for 20% of the $CaF_2$ fed to the reactor, whereby 80% of this feed is converted in the reactor.

The remaining gaseous mixture, at 170 g/min, is cooled (quenched) and analyzed to contain 118 g/min of CO, 2 g/min of $CF_4$, and 50 g/min of $COF_2$. The CO and $CF_4$ can be recycled to the reactor.

The material flow rates for this Example are shown in Table II.

TABLE II

| Component | Plasma Feed (g/min) | Liquid Product (g/min) | Exit Gases (g/min) |
|---|---|---|---|
| CO | 140 | | 117.9 |
| $CaF_2$ | 78 | 15.6 | |
| $COF_2$ | | | 49.6 |
| $CF_4$ | | | 2.1 |
| Calcium | | 30.0 | |
| CaO | | 2.8 | |
| Total | 218 | 48.4 | 169.6 |

Example 3

A different plasma reactor was used in the experiment forming the subject matter of this Example. The plasma torch is a Metco (Model MBN) torch and this torch is mounted across the top opening of a water cooled copper cylinder having an inner diameter of 2.54 cm and a length of 5.08 cm, to form the plasma reactor. The outlet end of the reactor communicates with a water-cooled heat exchanger.

The feed gas to the plasma torch consists of argon, fed to the torch at a flow rate of 7.5 liters (STP)/min, the torch operating at a current of 450 amps and at 33 volts, producing a power input of 14.8 KW. The argon plasma flame extends into the copper cylinder (reactor) via the inlet end of the reactor, and energy balance calculations indicate the temperature of the plasma flame (bulk gas temperature) at the inlet end are about 10,000K. At the reactor inlet, $SiF_4$ is injected into the plasma flame at 1.9 liters (STP)/min through injection nozzles sized to promote sonic velocities and good mixing of the $SiF_4$ in the plasma flame to promote dissociation of the $SiF_4$ and formation of free fluorine. CO is injected into the reactor rate of 30 liters (STP)/min 5.08 cm downstream from the reactor inlet to react with the free fluorine and to quench the plasma flame to favor the formation of $COF_2$ rather than $CF_4$. The CO is at room temperature when injected into the reactor, so that simultaneous with the reaction between CO and F, the CO together with the water-cooled reactor wall rapidly quenches the resultant gaseous reaction product.

The gaseous reaction product is quenched to ambient temperature (15°–20° C.) for the purpose of infrared analysis, and this quenching is accomplished by passing the product gas through the water-cooled heat exchanger. Samples of the product gas are collected in bags of TEDLAR® polyvinyl fluoride for infrared analysis. Fluorocarbon yields in the product gas are 94 mol % $COF_2$ and 6 mol % $CF_4$.

What is claimed is:

1. Process for the manufacture of $COF_2$ comprising reacting fluorine-containing compound having a molecular weight greater than 20 with CO and obtaining as a result thereof said $COF_2$, said reacting being energized by a plasma.

2. The process of claim 1 wherein the reaction is carried out at a temperature of at least 1500° C.

3. The process of claim 1 wherein the reaction is carried out at a temperature of 3500° C. to 6000° C.

4. The process of claim 1 wherein an excess amount of CO is present in the reaction.

5. The process of claim 1 wherein said compound is organic or inorganic.

6. The process of claim 5 wherein said inorganic compound is at least one metal fluoride.

7. The process of claim 6 wherein metal from said metal fluoride is also obtained, and separating said metal and said $COF_2$ one from the other.

8. The process of claim 6 wherein said metal fluoride is silicon fluoride.

9. The process of claim 6 wherein said metal fluoride is calcium fluoride.

10. The process of claim 6 wherein the reaction temperature is such to cause dissociation of said metal fluoride and said CO remains essentially undissociated.

11. The process of claim 1 wherein the yield of $COF_2$ is at least 60%.

12. The process of claim 2 wherein the reaction produces a gaseous reaction mixture, and quenching said gaseous reaction mixture obtain said $COF_2$.

13. Process comprising contacting and reacting fluorine-containing compound having a molecular weight greater than 20 with CO, said reacting being energized by a plasma to liberate fluorine from said fluorine-containing compound to form a gaseous reaction mixture which is capable of being quenched to obtain $COF_2$.

14. The process of claim 13 wherein the reaction is carried out by energizing either the fluorine-containing compound having a molecular weight greater than 20 or CO or both or by feeding energized inert gas to the reaction.

15. The process of claim 14 wherein the energizing is by plasma excitation.

16. The process of claim 13 and quenching said reaction mixture.

17. The process of claim 1 wherein $CF_4$ is co-produced with said $COF_2$.

18. The process of claim 1 wherein said fluorine-containing compound is free of hydrogen.

19. The process of claim 6 wherein said fluorine-containing compound is fluorosilicate.

* * * * *

UNITED STATES PATENT AND TRADEMARK OFFICE
CERTIFICATE OF CORRECTION

PATENT NO. : 5,648,530
DATED : July 15, 1997
INVENTOR(S) : James Lang Webster

It is certified that error appears in the above-identified patent and that said Letters Patent is hereby corrected as shown below:

```
On the title page, after item [76], insert the following:
[73]  Assignee:  E.I. du Pont de Nemours and Company,
                 Wilmington, Del.
```

Signed and Sealed this

Seventeenth Day of February, 1998

Attest:

BRUCE LEHMAN

*Attesting Officer*  *Commissioner of Patents and Trademarks*